United States Patent [19]
Kimura et al.

[11] Patent Number: 5,418,171
[45] Date of Patent: May 23, 1995

[54] METHOD FOR DETECTING A TARGET ANALYTE IN A SAMPLE

[75] Inventors: Fumio Kimura; Naohisa Koizumi; Koichi Matsuo; Minoru Aoyagi, all of Yokohama; Kiyomi Harakawa, Chuo, all of Japan

[73] Assignee: Meiji Seika Kabushiki Kaisha, Japan

[21] Appl. No.: 949,624

[22] PCT Filed: Mar. 30, 1992

[86] PCT No.: PCT/JP91/00394
§ 371 Date: Nov. 30, 1992
§ 102(e) Date: Nov. 30, 1992

[87] PCT Pub. No.: WO92/17782
PCT Pub. Date: Oct. 15, 1992

[30] Foreign Application Priority Data

Mar. 28, 1991 [JP] Japan .................. 3-064433

[51] Int. Cl.[6] .............. G01N 33/537; G01N 33/538; G01N 33/543; G01N 33/553
[52] U.S. Cl. .................. 436/518; 422/56; 422/57; 422/58; 435/7.92; 435/7.94; 435/810; 436/165; 436/169; 436/524; 436/525; 436/528; 436/530; 436/536; 436/538; 436/540; 436/541; 436/805; 436/807; 436/809; 436/810
[58] Field of Search ............. 436/540, 541, 530, 501, 436/518, 524, 525, 528, 536, 538, 165, 169, 805, 807, 809, 810; 435/7.92, 6, 7.94, 7.95, 7.9, 975, 970, 810; 422/57, 58, 60, 56, 101

[56] References Cited

U.S. PATENT DOCUMENTS 4,146,365  3/1979  Kay et al. ................... 424/57
4,727,019  2/1988  Valkirs et al. ............... 435/5
5,145,789  9/1992  Cortiv et al. ................ 436/530

FOREIGN PATENT DOCUMENTS 0295069  12/1988  European Pat. Off. .

OTHER PUBLICATIONS

Patent Abstracts of Japan; vol. 12, No. 380 (P-769) 12 Oct. 1988; abstract.

Primary Examiner—Toni R. Scheiner
Assistant Examiner—Christopher L. Chin
Attorney, Agent, or Firm—Wenderoth, Lind & Ponack

[57] ABSTRACT

The present invention relates to an apparatus for determining the presence or absence of a target analyte in a liquid sample, comprising:
(i) a container capable of accommodating the liquid sample and having a transparent portion; and
(ii) an insertion member which is capable of being inserted into the container comprising;
a porous member which has a main surface and a reverse surface and which has on the main surface a substance capable of specifically binding to the target analyte; and
an absorbent bonded to the reverse surface of the porous member;
the porous member being supported in the insertion member whereby, when the insertion member is inserted into the container, the main surface can be observed from the outside of the container through the transparent portion of the vessel and the liquid sample is absorbed into the absorbent through the porous member.

According to the analyzer of the present invention, the presence or absence of a target analyte in a sample can be easily determined. The analyzer of the present invention is sanitary and easy to handle.

5 Claims, 5 Drawing Sheets

METHOD FOR DETECTING A TARGET ANALYTE IN A SAMPLE

BACKGROUND OF THE INVENTION

1. Field of the Invention

The present invention relates to an analyzer which can easily determine the presence or absence of a target analyte in a sample through immunoassay or the like.

2. Background Art

The presence or absence of a target analyte in a sample has hitherto been determined by bringing the sample into contact with a substance capable of specifically binding to the target analyte and detecting a binding reaction between the target analyte and the substance. Examples of such a technique include in immunological technique by virtue of an antigen-antibody reaction and a hybridization technique for determining the presence or absence of a target sequence through a hybridization with a specific oligonucleotide.

With respect to the immunological technique, various methods are known wherein a liquid sample is brought into contact with a carrier having a surface on which an antibody capable of specifically binding to an antigen has been immobilized and a labelled antibody is allowed to treat the carrier, thereby determining the presence of an antigen in the liquid sample.

For example, Japanese Patent Laid-Open No. 127160/1988 discloses an apparatus wherein a membrane having an antibody bound thereto in a spot form is put on the top surface of a cylindrical container and the lower portion is filled with a highly hygroscopic substance. In this apparatus, at the outset, a liquid sample is added, and an antibody labelled with a gold colloid particle is dropwise added thereto. If the liquid sample contains an antigen in a detectable concentration or more, a reddish purple spot is observed.

Similar apparatuses are disclosed in Japanese Patent Publication Nos. 502214/1986 and 25551/1988. In these apparatuses, it is necessary to conduct two steps, i.e., the step of adding a liquid sample to the membrane portion for allowing the liquid sample to be absorbed into the membrane and the step of dropwise adding a labelled antibody solution. Thus, the procedure may become complicate. Further, in these apparatuses, the membrane easily dries. It is unfavorable for the membrane to easily dry, because this gives rise to a difference in the results between immediately after the reaction and after drying. Further, when the liquid sample is a urine or feces suspension or the like, an apparatus having the surface of the membrane which is exposed to air even after the reaction is unsanitary. Moreover, the apparatus having the surface of the membrane which is exposed to air is unsuitable for transportation.

SUMMARY OF THE INVENTION

An object of the present invention is to provide a simple analyzer.

Another object of the present invention is to provide an apparatus having a surface of a membrane which does not easily dry after a reaction, whereby results of reaction are less susceptible to change with the elapse of time and whereby the apparatus is sanitary and easy to transport.

The analyzer according to the present invention relates to an apparatus for determining the presence or absence of a target analyte in a liquid sample, comprising:

(i) a container capable of accommodating the liquid sample and having a transparent portion; and (ii) an insertion member which is capable of being inserted into the container comprising;

a porous member which has a main surface and a reverse surface and which has on the main surface a substance capable of specifically binding to the target analyte; and an absorbent bonded to the reverse surface of the porous member;

the porous member being supported in the insertion member whereby, when the insertion member is inserted into the container, the main surface can be observed from the Outside of the container through the transparent portion of the vessel and the liquid sample is absorbed into the absorbent through the porous member.

According to the analyzer of the present invention, a reaction between a target analyte and a substance capable specifically binding to the target substance can be easily observed Outside the apparatus.

BRIEF DESCRIPTION OF THE DRAWINGS

FIG. 3($b$) is a perspective view of an assembled analyzer comprising container 1 and insertion member 2 that is inserted into and coupled with container 1;

FIG. 3($c$) is a bottom end view of the assembled analyzer of FIG. 3($b$);

BEST MODE FOR CARRYING OUT THE INVENTION

Figure 1:
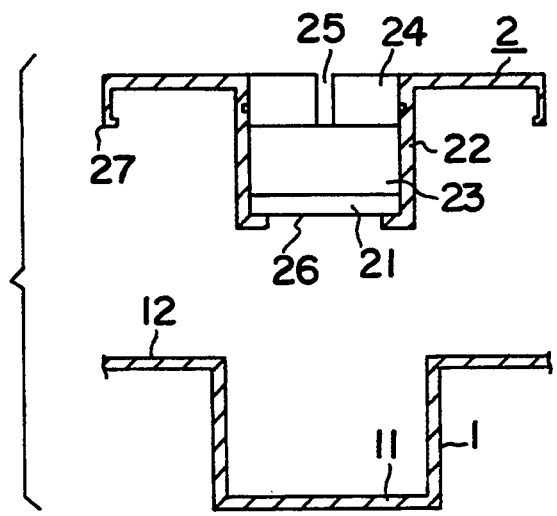
FIG. 1 is a sectional view of a preferred embodiment of the analyzer according to the present invention.

A preferred embodiment of the analyzer according to the present invention is shown in FIG. 1. FIG. 1 is a sectional view of the analyzer according to the present invention. A container 1 comprises a cylindrical vessel portion comprising a transparent material, for example, a resin, and an end 12 provided on the opening of the vessel portion. The whole container 1 may be transparent. Alternatively, the bottom portion 11 alone may transparent. An insertion member 2 comprises a supporting member 22 which is a cylinder having a barrel portion having a opening portion 26 and serves also as a body of the insertion member 2, a membrane 21 inserted into the barrel portion, an absorbent 23 in physical contact with the membrane 21 and a fixing member 24 having a vent hole 25 for fixing the membrane 21 to the absorbent 23. The insertion member 2 is capable of being inserted into the container 1. The insertion member 2 is provided with a protrusion 27 for stably fixing the insertion member 2 to the container when the insertion member 2 is inserted into the container 1. The protrusion 27 is engaged with the end 12 of the container 1 when the insertion member 2 is inserted into the container 1.

Figure 2:
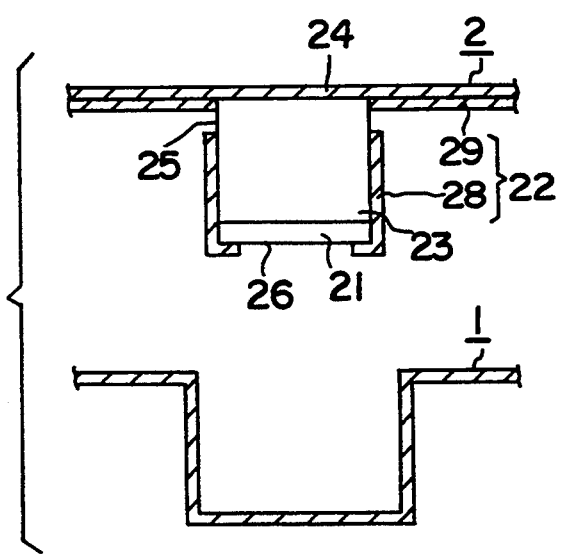
FIG. 2 is a sectional view of another preferred embodiment of the analyzer according to the present invention.

Another preferred embodiment of the analyzer according to the present invention is shown in FIG. 2. The members having the same function as that shown in FIG. 1 are designated by the same numerals. In the apparatus shown in FIG. 2, the supporting member 22 of the insertion member 2 comprises a barrel portion 28 in a cylindrical form and a flat plate portion 29 connected to the opening of the barrel portion 28. An opening portion 26 is provided at the bottom of the barrel portion. A vent hole 25 is provided on the side of the barrel portion 28. A membrane 21 is inserted into the bottom of the barrel portion 28, and an absorbent 23 is inserted into the barrel portion 28 so that it comes into physical contact with the membrane 21. The membrane 21 and the absorbent 23 are fixed to the barrel portion 28 of the supporting member 22 by bonding a fixing plate 24 to the supporting member 22 at its flat plate portion.

The membrane 21 comprises a porous material. The term "porous" used herein is intended to mean that the membrane 21 has a water permeability to such an extent that water permeates through the membrane 21 and easily reaches the absorbent 23. Preferred examples of the material for the membrane 21 include nitrocellulose, cellulose mixed ester, polyvinylidene fluoride and nylon 66. The absorbent. 23 comprises a material capable of absorbing water which has been passed through the membrane 21. Preferred examples thereof include filter paper, filter paper powder, coaster paper, chip board paper, felt, nonwoven fabric, absorbent cotton, sodium polyacrylate, rubber and high polymer.

In the embodiment shown in FIG. 1, a substance which is capable of specifically binding to the target analyte is carried on the main surface of the membrane 21 which faces on the side of the opening portion 26.

There is no particular limitation on the kind of the target analyte which can determine the presence or absence by the analyzer according to the present invention so far as a substance capable of specifically binding to the target analyte can be provided and the presence or absence of a bond between the target analyte and the substance capable of specifically binding to the target analyte can be determined. Preferred examples of the combination of a target analyte with a substance capable of specifically binding to the target analyte include a combination of an antigen with an antibody and a combination of two hybridizable nucleotide sequences.

Figure 3A:
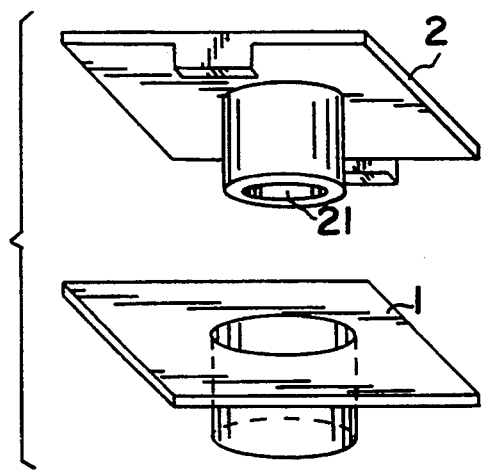
FIG. 3($a$) is a perspective view of a further preferred embodiment of an analyzer according to the present invention comprising insertion member 2 provided with member 21, said member 21 having a substance capable of specifically binding to the target analyte and container 1.
Figure 3B:
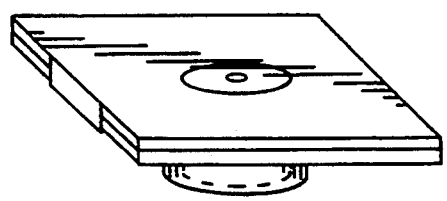
Figure 3C:
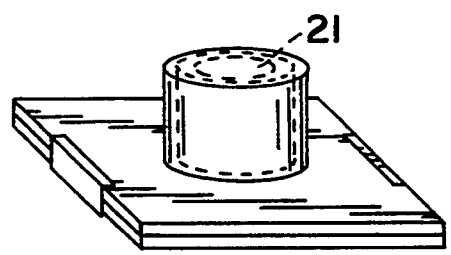

The procedure of the determination of the presence or absence of the target analyte in the sample by use of the analyzer shown in FIG. 1 will now be described with reference to FIG. 3.

First, a liquid sample to be analyzed is poured into a container 1. An insertion member 2 provided with a membrane 21 having a substance capable of specifically binding to the target analyte is, then, inserted into the container 1 (see FIG. 3 (a)), and a protrusion 27 is engaged with an end 12 to connect the container 1 to the insertion member 2 (see FIG. 3 (b)). When the insertion member 2 is inserted into the container 1, the liquid sample within the container 1 is absorbed into the absorbent 23 through the membrane 21. If the target analyte is present in the liquid sample, the target analyte in the liquid sample is bound to the substance capable of specifically binding to the target analyte on the membrane 21 and stays on the membrane 21. When a labelled substance capable of emitting a signal, preferably a visible signal, in response to the presence or absence of the binding reaction is presented, it becomes possible to learn whether or not the target analyte is present on the membrane 21. In the present invention, as shown in FIG. 3 (c), since the container 1 in its entirety or at its bottom portion is transparent, a signal emitted on the membrane 21 by this labelled substance can be easily observed from the outside of the container 1.

In the analyzer according to the present invention, it is possible to prevent the membrane 21 from drying since the membrane 21 is covered with the container 1. Therefore, the results of the test can be judged even after the elapse of time. Further, since the liquid sample is absorbed into the absorbent 23 and the container 1 is stably connected to the insertion member 2, the liquid sample does not leak out. The analyzer is sanitary and can be easily carried.

The determination of the presence or absence of an target analyte by use of an antigen-antibody reaction will now be described in more detail.

When an antigen-antibody reaction is employed, the target analyte to be detected may be any of an antigen and an antibody. Specific examples of the target analyte include hemoglobin, HCG, anti-HIV antibody, anti-HCV antibody, HBV antibody, HIV antigen, HCV antigen, HBV antigen and LH.

For example, when the presence or absence of a certain antigen is determined by "sandwich immunoassay", a first antibody against the antigen is carried on the membrane 21. The antibody may be carried on the membrane 21 through a physical adsorption or a chemical bond. The method of binding the antibody may be properly selected depending upon a material of the membrane 21.

Further, in the case of the sandwich immunoassay, a second antibody against the antigen should be provide. The second antibody may be directly or indirectly labelled. Although there is no particular limitation on the method of labelling the second antibody, the antibody is preferably labelled with a metallic particle, a colored latex particle, blue dextran, a microorganism, a pigment, liposome, an enzyme or the like. In the present invention, it is preferred to use a method wherein an antibody is labelled with colloidal gold (Horisberger and Rossert, J. Histochem, Cytochem, 25, 295–305 (1877) and Japanese Patent Laid-Open No. 25553/1988 and 32169 (1989).

The first antibody and second antibody may be the same or different. For example, it is also possible to use a polyclonal antibody and a monoclonal antibody respectively as the first antibody and the second antibody. It is also possible to use a combination of monoclonal antibodies different from each other in an epitope.

The presence or absence of the antigen in the sample is determined with an analyzer shown in FIG. 1 according to the following procedure. First, a liquid sample is prepared by a method such as dilution of a sample derived from an organism, and the second antibody is added to the resultant solution. The resultant liquid sample containing the second antibody is placed in the container 1. An insertion member 2 provided with a membrane 21 having the first antibody carried thereon is inserted into the container 1 containing the liquid sample with the antibody.

If a target antigen is present in the liquid sample, the target analyte binds to the first antibody on the membrane 21 and further the second antibody in the liquid sample. The antibody-antigen reaction causes the labelling substance on the membrane 21 to emit a signal. This signal can be observed from the outside of the container 1 through the transparent portion of the container 1. For example, when the second antibody is labelled with colloidal gold, the presence of an antigen in the liquid sample causes the membrane 21 to be colored to reddish purple. The coloration can be easily observed through the transparent portion of the container 1.

In the above procedure according to the present invention, a step of washing an unreacted antigen is omitted although the step is usually conducted in the sandwich immunoassay after the reaction of the first antibody with the antigen. It is a matter of course that it is possible to use a method which includes the steps of bringing the membrane 21 into contact with a liquid sample which does not include the second antibody, bringing water into contact with the membrane 21 to wash the membrane and bringing a solution containing the second antibody into contact with the membrane 21. In the apparatus of the present invention, however, if the specificity of the Second antibody is more selective, it is possible to determine the presence or absence of an antigen as the target analyte without the above washing step. The omission of the washing step is preferred also from the viewpoint of simplification of the assay procedure.

A still preferred example with the analyzer according to the present invention is to determine hemoglobin in a stool. A sample solution containing the dejection diluted by a factor of 50 to 1000 is prepared by suspending the dejection in water. A polyclonal antibody against hemoglobin is used as the first antibody and carried on the membrane 21. A hemoglobin monoclonal antibody labelled with collidal gold is used as the second antibody. The second antibody is mixed with the sample solution, and the above procedure according to the present invention is conducted to determine the presence of hemoglobin in the dejection.

Figure 4A:
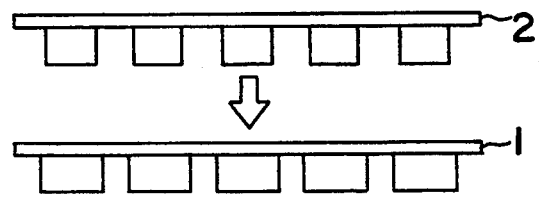
Figure 4B:
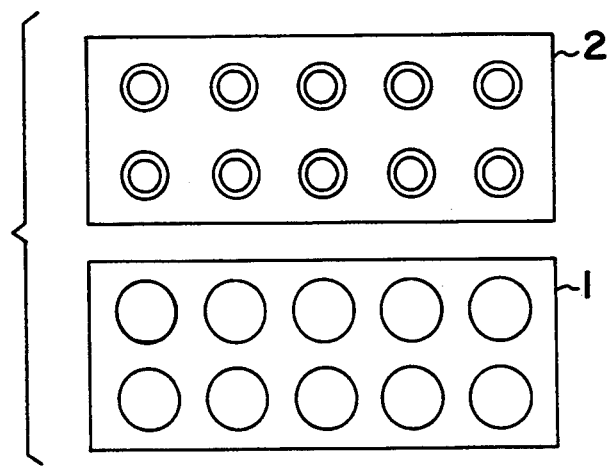
Figure 4C:
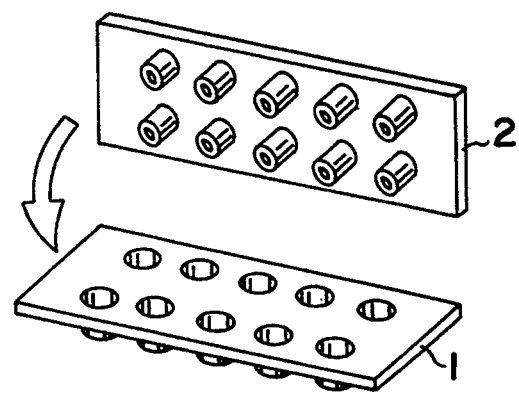
Figure 5A:
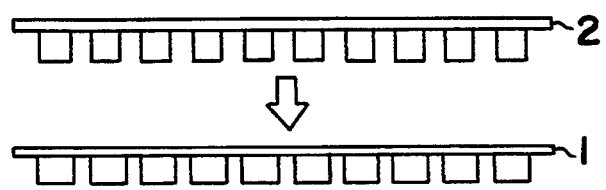
Figure 5B:
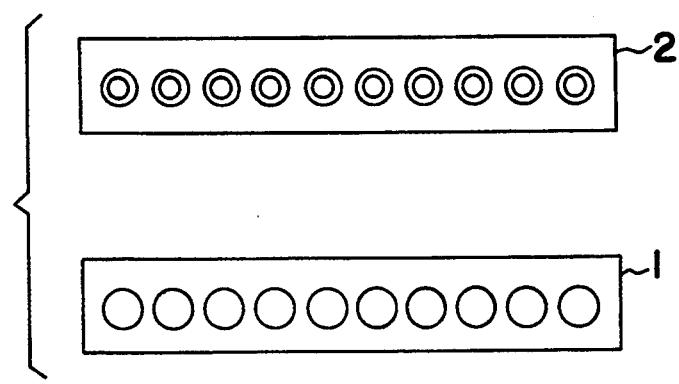
Figure 6A:
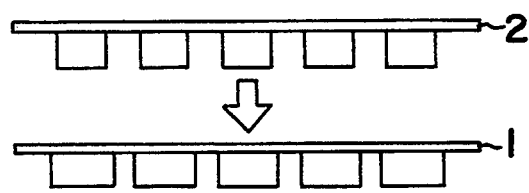
Figure 6B:
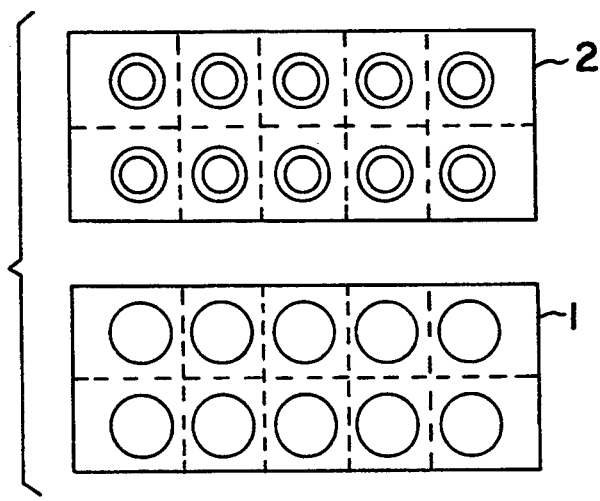

According to a preferred embodiment of the present invention, the analyzer according to the present invention may comprise a plurality of containers 1 connected to and integrated with each other and a plurality of insertion members 2 connected to and integrated with each other. For example, as shown in FIGS. 4 (*a*) and (*b*) are respectively a sectional view and a plan view of the analytical apparatus according to the present invention Comprising a plurality of containers 1 connected to each other in two rows and a plurality of insertion members 2 connected to each other in two rows. As shown in FIG. 4 (*c*), an analyzer enables a plurality of samples to be simultaneously analyzed. FIGS. 5 (*a*) and (*b*) show an embodiment wherein the analyzer comprises a plurality of containers 1 in one row and a plurality of insertion members 2 in one row. As shown in FIG. 6, a cut line or a line may be provided so that a plurality of containers 1 connected to each other and a plurality of insertion members 2 connected to each other can be easily separated one by one or plural by plural.

The present invention will now be described in more detail with reference to the following Examples, though the present invention is not limited to these Examples.

EXAMPLE 1

(1) Preparation Of Colloidal Gold

A 10% chloroaurate solution ($HAuCl_4.4H_2O$) was added to 500 ml of distilled water of 95° C. with stirring. One min after the addition, 5 ml of a 2 % sodium citrate solution was added thereto, stirring was continued for additional 20 min, and the reaction mixture was cooled to 30° C. After cooling a pH value of the reaction mixture was adjusted to 7.0 with a 0.1M potassium carbonate solution. 1 ml of 1% PEG 20000 was added to the mixture as a stabilizer. The mixture was stirred for 10 min and filtered by means of a 0.22 μm filter manufactured by Millipore.

(2) Preparation Of Anti-Human Hemoglobin Monoclonal antibody labelled with colloidal gold Anti-human hemoglobin monoclonal antibody MSU-110 (manufactured by Nippon Biotest Laboratory) was diluted with 10 mM HEPES (pH:7.1) to a concentration of 200 μg/ml. 3 ml of the solution and 30 ml of the colloidal gold solution prepared in part (1) was placed in a centrifugation tube and sufficiently stirred. Then, 3.3 ml of an A1 buffer 10 mM HEPES, 0.3M D-mannitol, 0.05 % PEG 20000, 0.1% BSA, pH 7.1)was added to the tube. The mixture was stirred for one hour, and was centrifuged at 10° C. and 9000 rpm for 10 min. The supernatant was placed in another centrifugation tube and centrifuged at 10° C. and 15000 rpm for 30 min. The above procedure was repeated twice, and 10 ml of the A1 buffer was added to the resultant precipitate.

(3) Preparation of antibody-bound membrane

Anti-human hemoglobin rabbit polyclonal antibody (manufactured by DAKO PATTS) was diluted with PBS (0.9% NaCl, 10 mM phosphate buffer, pH 7.2) so that the concentration was 1 mg/ml. A nitrocellulose membrane (manufactured by Bio Rad) having a size of 1 cm×1 cm was blotted with 3 μl of the solution. After air drying, the membrane was immersed in 1% BSA-added PBS at 37° C. for one hour and then air-dried.

(4) Measurement of human hemoglobin and change with time

Human hemoglobin (manufactured by SIGMA) was dissolved in A1 buffer to prepare human hemoglobin solutions having concentrations of 0 μg/ml, 0.05 μg/ml and 0.2 μg/ml. 60 μl of these human hemoglobin solutions and 60 μl of the anti-human hemoglobin monoclonal antibody labelled With colloidal gold prepared in part (2) were added to the container 1 shown in FIG. 1, and mixing was conducted. An insertion member 2 shown in FIG. 1 having, carried thereon as a membrane 21, an antibody-bond membrane prepared in part (3) was prepared. This insertion member was inserted into and put on top of the container. 3 min after the inserting member was put on top of the container, the container and the insertion member were reversed and the results of reaction on the surface of the antibody-bound membrane were observed for additional 60 min. the results were as given in Table 1. Separately, 3 min after the insertion member was put on top of the container, the insertion member was put off from the container and reversed, the results of reaction on the surface of the antibody-bound membrane were observed for additional 60 min. The results were as given in Table 2.

TABLE 1

| Hemoglobin concentration | Reaction time (min) | | | |
|---|---|---|---|---|
| (μg/ml) | 3 | 15 | 30 | 60 |
| 0 | − | − | − | − |
| 0.05 | ± | ± | ± | ± |
| 0.2 | + | + | + | + |

TABLE 2

| Hemoglobin concentration (μg/ml) | Reaction time (min) | | | |
|---|---|---|---|---|
| | 3 | 15 | 30 | 60 |
| 0 | − | − | * | * |
| 0.05 | ± | ± | * | * |
| 0.2 | + | + | * | * |

The evaluation was conducted by observing the intensity of coloration to reddish purple of the colloidal gold with the naked eye.

In the table,

−: no coloration was observed.

±: slight coloration was observed.

+: clear coloration was observed.

*: heterogeneous coloration occurred when the surface of the membrane was dried, which made it difficult to conduct the judgment.

We claim:

1. A method for detecting the presence or absence of a target analyte in a sample by using a first substance and a second substance both of which are capable of specifically binding to the target analyte, comprising the steps of:

forming a mixture by mixing a liquid sample containing the sample and a solution containing the first substance, wherein the first substance is labelled, providing an apparatus comprising (a) a container capable of accommodating said mixture, the container having a transparent portion, (b) an insertion member capable of being inserted into and integrally coupled with the container comprising;

(i) a supporting member with a barrel portion that fits into said container, said barrel portion containing a porous member which has two surfaces, a first surface that contacts the mixture in said container and a second surface opposite said first surface, wherein the second substance is immobilized on the first surface of the porous member; and [(ii)]an absorbent contacting the second surface of the porous member; and (ii) a vent hole located either in said barrel portion or in said supporting member above the absorbent;

pouring the mixture into said container, coupling said container and said insertion member of said apparatus by inserting the insertion member into the container, and without washing said porous membrane, detecting an occurrence of a reaction between the target analyte and the first and second substances through the signal emitted from the labelled first substance by observing the main surface of the porous member through the transparent portion of the container.

2. The method according to claim 1, wherein the porous member is a membrane.

3. The method according to claim 1, wherein the target analyte is an antigen and the first and second substances are antibodies.

4. The method according to claim 1, wherein the first substance is labelled with a metallic particle, a colored latex particle, blue dextran, a microorganism, a pigment, liposome, or an enzyme.

5. The method according to claim 4, wherein the metallic particle is colloidal gold, the occurrence of the reaction between the target analyte and the first and second substances are visually observed through the transparent portion of the container.

* * * * *